United States Patent
Zaunbrecher

[19]
[11] Patent Number: 5,876,706
[45] Date of Patent: *Mar. 2, 1999

[54] AIR FRESHENER DISPENSER DEVICE WITH TAPER CANDLE FEATURE

[75] Inventor: Judith R. Zaunbrecher, Racine, Wis.

[73] Assignee: S. C. Johnson & Son, INc., Racine, Wis.

[*] Notice: This patent issued on a continued prosecution application filed under 37 CFR 1.53(d), and is subject to the twenty year patent term provisions of 35 U.S.C. 154(a)(2).

[21] Appl. No.: 912,413

[22] Filed: Aug. 18, 1997

[51] Int. Cl.$^6$ ................................................. A61L 9/015
[52] U.S. Cl. .......................................... 424/76.1; 424/76.2
[58] Field of Search ...................... 424/76.1, 7.2

[56] References Cited

U.S. PATENT DOCUMENTS

| | | | |
|---|---|---|---|
| 2,090,297 | 8/1937 | Knoche | 21/111 |
| 2,379,250 | 6/1945 | Muskat et al. | 260/463 |
| 2,415,040 | 1/1947 | Rust | 106/197 |
| 2,679,069 | 5/1954 | Keogh | 18/13 |
| 2,818,615 | 1/1958 | Burness | 21/111 |
| 2,829,511 | 4/1958 | Oesterle et al. | 67/22 |
| 3,175,876 | 3/1965 | Fredericks | 21/116 |
| 3,332,428 | 7/1967 | Mold et al. | 131/17 |
| 3,461,197 | 8/1969 | Lemelson | 264/172 |
| 3,499,452 | 3/1970 | Kallianos et al. | 131/17 |
| 3,560,122 | 2/1971 | Cassar | 431/288 |
| 3,705,890 | 12/1972 | Barker et al. | 260/228 |
| 3,898,039 | 8/1975 | Lin | 21/108 |
| 4,092,988 | 6/1978 | Van Auken et al. | 131/17 |
| 4,099,916 | 7/1978 | Gardner et al. | 21/116 |
| 4,155,979 | 5/1979 | Powell | 422/126 |
| 4,215,719 | 8/1980 | Newman | 422/126 |
| 4,237,097 | 12/1980 | McDuffie | 422/126 |
| 4,278,658 | 7/1981 | Hooper et al. | 424/65 |
| 4,324,763 | 4/1982 | Jarman | 422/116 |
| 4,334,853 | 6/1982 | Gardner | 431/2 |
| 4,435,348 | 3/1984 | Standley | 264/174 |
| 4,449,987 | 5/1984 | Lindauer | 44/7.5 |
| 4,507,077 | 3/1985 | Sapper | 431/228 |
| 4,568,270 | 2/1986 | Marcus et al. | 431/288 |
| 4,663,315 | 5/1987 | Hasegawa et al. | 514/86 |
| 4,708,851 | 11/1987 | Loren | 422/123 |
| 4,713,139 | 12/1987 | Ganga | 156/500 |
| 4,843,061 | 6/1989 | Broekhof et al. | 512/22 |
| 5,068,321 | 11/1991 | Buysch et al. | 53/32 |
| 5,069,231 | 12/1991 | Rutherford | 131/335 |
| 5,081,104 | 1/1992 | Orson, Sr. | 512/3 |
| 5,313,002 | 5/1994 | DeHeij et al. | 568/64 |
| 5,529,652 | 6/1996 | Asai et al. | 156/180 |
| 5,538,018 | 7/1996 | Chan et al. | 131/276 |
| 5,569,779 | 10/1996 | Sabahi et al. | 560/190 |
| 5,645,845 | 7/1997 | Neumann et al. | 424/405 |

Primary Examiner—Thurman K. Page
Assistant Examiner—Kathryne E. Shelborne
Attorney, Agent, or Firm—J. William Frank, III

[57] ABSTRACT

This invention provides an air freshener dispenser device which has a taper candle feature. The taper candle consists of (1) a combustible encapsulant ingredient, and (2) a cellulosic matrix (such as cotton or rayon yarn) which has a content of a chemically-bound air freshener constituent such as geraniol, citronellal or menthol. The linkage between the air freshener and cellulosic matrix can be an ether or carbonate ester covalent bond. When the taper candle is ignited, it burns with a flame combustion, and there is a controlled release of the air freshener constituent into the atmosphere.

38 Claims, 1 Drawing Sheet

Fig.1
Fig.3
Fig.2
Fig.4
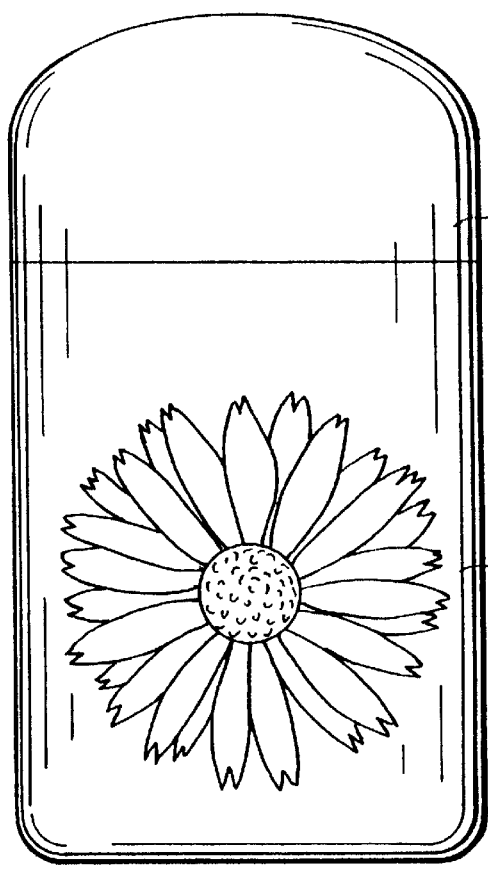
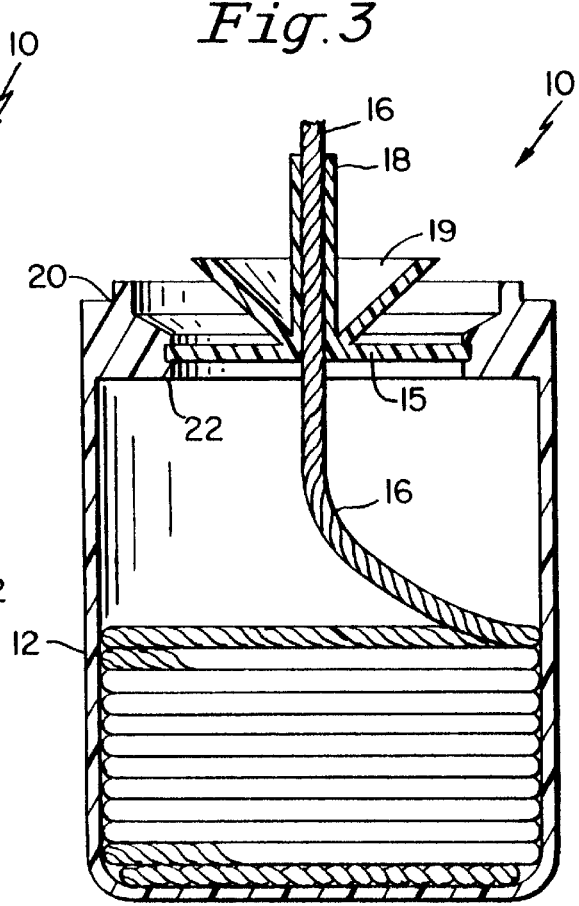
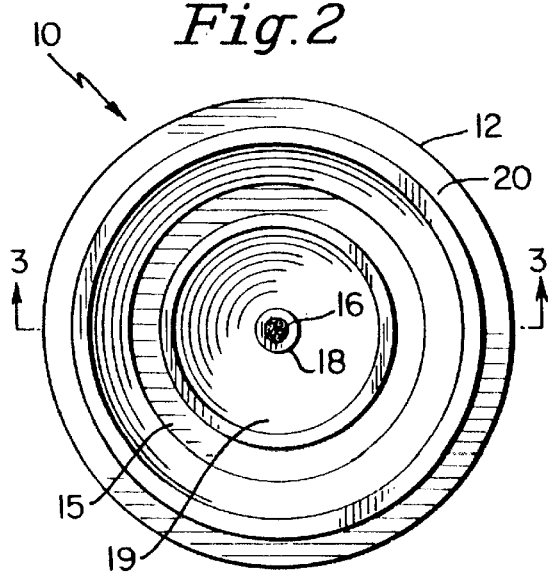
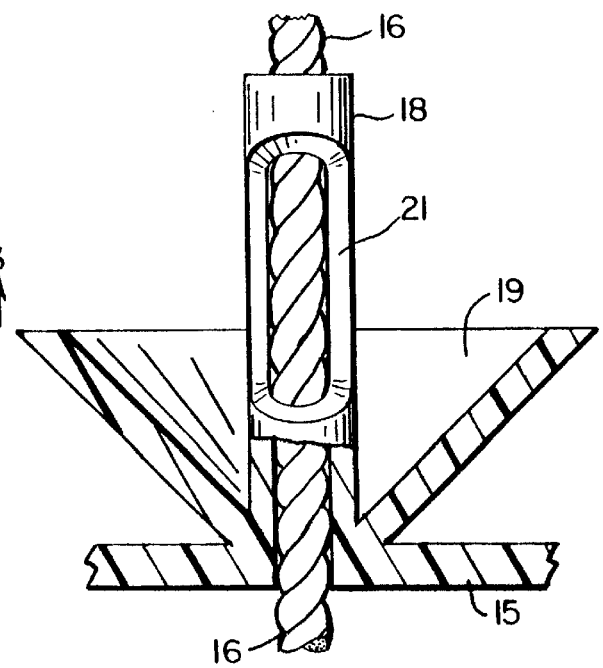

AIR FRESHENER DISPENSER DEVICE WITH TAPER CANDLE FEATURE

CROSS-REFERENCE TO RELATED PATENT APPLICATION

The subject matter of this patent application is related to that disclosed in copending U.S. patent application AIR FRESHENER DISPENSER DEVICE WITH COMBUSTIBLE TAPER STRAND FEATURE, Attorney Docket No. J-2614, application No. 08/912,852, filed along with this application.

BACKGROUND OF THE INVENTION

This invention generally relates to dispensers of vaporizable media. More specifically, this invention relates to a candle-type product for dispensing a fragrance or active ingredient in the form of a vapor for air freshening in an enclosed environment.

Candles have been known and used since early civilization. A typical candle is formed of a solid or semi-solid body of wax such as paraffin wax or beeswax, and it contains an axially embedded combustible fibrous wick.

When the wick of a candle is lit, the generated heat melts the solid wax, and the resulting liquid flows up the wick by capillary action and is combusted.

More recently candles have been developed that appeal to the olfactory as well as the visual sense. This type of candle usually incorporates a fragrance oil in the wax body. As the wax is melted in a lighted candle, there is a release of the fragrance oil from the liquified wax pool.

Conventional fragrance candles have drawbacks because of cost and other considerations. The incorporation of fragrance oil in candle wax is difficult to achieve in a quantity which ensures the release of a suitable level of fragrance into the atmosphere during candle burning. Further, the incorporated fragrance tends to migrate and volatilize from the wax body prematurely. The fragrance also softens the wax body, and there is an undesirable loss of rigidity in the candle structure.

There is continuing interest in the development of improved fragrance and other types of air freshener candle products.

Accordingly, it is an object of this invention to provide an air freshener dispenser device with a candle means which releases air freshener into the atmosphere only under the pyrolysis conditions of candle combustion.

It is another object of this invention to provide a taper candle product which has a content of chemically-bound air freshener constituent.

It is a further object of this invention to provide a taper candle product which can be produced by a continuous molding process.

Other objects and advantages of the present invention shall become apparent from the accompanying drawings and examples.

Publications of background interest relative to the present invention include U.S. Pat. Nos. 2,090,297; 2,379,250; 2,818,615; 2,829,511; 3,332,428; 3,499,452; 3,560,122; 3,705,890; 3,898,039; 4,092,988; 4,568,270; 5,538,018; and 5,569,779; incorporated by reference.

U.S. Pat. No. 2,818,615 describes a deodorizer device in which a combustible cord is impregnated with an air freshener, and the air freshener is released when the cord is ignited.

U.S. Pat. No. 2,829,511 describes a candle wick structure composed of a core strand of cellulose acetate in combination with an outer web of cotton fibers.

U.S. Pat. No. 5,538,018 describes a flavorant-release additive which is a cellulose derivative that is incorporated into a cigarette paper wrapper.

SUMMARY OF THE INVENTION

One or more objects of the present invention are accomplished by the provision of an air freshener dispenser device which comprises:

(1) a container with an interior storage chamber;
(2) a taper candle comprising
   (a) a cellulosic matrix having a content of chemically-bound air freshener constituent, and
   (b) combustible encapsulant ingredient, and which taper candle is disposed within the container storage chamber;
(3) a closure means which forms a partition across the top section of the container; and
(4) a narrow bore tube which is supported by the partition in a vertically extended position, and which has access through the partition to the container storage chamber; wherein the vertical tube is adapted to receive and guide passage of the taper candle from the container storage chamber, and to support an exposed end-section of the taper candle which extends upward from the tube; and wherein the taper candle is adapted for release of the chemically-bound air freshener constituent into the atmosphere when the taper candle is combusted.

In another embodiment this invention provides a taper candle product comprising
(a) a cellulosic matrix having a content of chemically-bound air freshener constituent, and
(b) combustible encapsulant ingredient; wherein the taper candle is adapted for release of the chemically-bound air freshener constituent into the atmosphere when the taper candle is combusted.

DESCRIPTION OF THE DRAWINGS

FIG. 1 is an elevational side view of an invention air freshener dispenser device with a lid cover in place.

FIG. 2 is a plan top view of a FIG. 1 air freshener dispenser device without a lid cover.

FIG. 3 is a cross-sectional side view of a FIG. 2 air freshener dispenser device taken along line 3—3.

FIG. 4 is an enlarged elevational side view of the vertical tube feature of a FIG. 3 air freshener dispenser device.

DESCRIPTION OF THE PREFERRED EMBODIMENTS

FIG. 1 is an elevational side view of invention air freshener dispenser device 10 before it is in an operational mode.

As illustrated, dispenser device 10 of FIG. 1 is constructed of molded plastic container 12 and dome-shaped lid cover 14. Container 12 and lid cover 14 can be injection or thermoform molded from a polymer such as polyethylene, polypropylene, polystyrene, polyvinyl chloride, polyvinyl acetate, cellulose acetate, polyamide, polymethacrylate, and the like.

Container 12 and lid cover 14 normally are disposable after the air freshener dispensing function has been completed. If container 12 and lid cover 14 are designed for extended use with air freshener refills, they can be constructed of glass, metal, wood, thermoset resin, or the like.

Air freshener dispenser device 10 in FIG. 1 typically has an annular cross-section with a height dimension between about 6–12 centimeters and a lateral dimension between about 2–5 centimeters.

FIG. 2 is a plan top view of FIG. 1 air freshener dispenser device 10 after dome-shaped lid cover 14 has been removed. Partition 15 is integrally in combination with vertical tube 18 and ash receptacle means 19. Taper candle 16 is disposed within vertical tube 18.

FIG. 3 is a cross-sectional side view of FIG. 2 air freshener dispenser device 10 taken along line 3—3. Taper candle 16 is guided from the container storage chamber and supported by vertical tube 18.

Taper candle 16 can have an annular cross-section with a diameter between about 2–8 millimeters, and a length of at least about 20 centimeters.

Taper candle 16 typically is comprised of cellulosic fibers which are twisted, plaited, woven, braided, or the like.

The cellulosic matrix of taper candle 16 can be obtained from sources such as cotton, linen, flax, hemp, wood pulp, and the like. The cellulosic matrix also can be in the form of a cellulosic derivative such as rayon, alkylated cellulose or esterified cellulose.

The term "cellulosic" as employed herein refers to a β-glucosidic polysaccharide corresponding to the formula:

$$[C_6H_7O_2(OH)_3]_n$$

where n is an integer which provides an average molecular weight between about 100,000–2,000,000.

Air freshener dispenser device 10 of FIG. 3 illustrates recess 20 for accommodating lid cover 14 when it is in place. Lid cover 14 also can be movably secured to container 12 so that it opens without being detached.

Interior extension rim 22 in FIG. 3 dispenser device 10 secures and supports partition 15. As illustrated in FIG. 3, partition 15 in combination with vertical tube 18 and ash receptacle means 19 is a retrievable unit. This access means facilitates a refill of the storage chamber with taper candle 16.

Partition 15, vertical tube 18 and ash receptacle means 19 can be formed of the same or different materials. Ash receptacle means 19 is an optional feature, since partition 15 can serve to collect residual ash.

The combination of partition 15, vertical tube 18 and ash receptacle means 19 can be a unitary structure which is composed of glass, metal or plastic. Because vertical tube 18 has contact with taper candle 16 when it is in a burning phase, vertical tube 18 preferably is a nonflammable or heat-resistant body.

After the extended end of taper candle 16 is ignited, it burns with a flame combustion down to the open end of vertical tube 18, where taper candle 16 then self-extinguishes.

FIG. 4 is an enlarged elevational side view of vertical tube 18 which is shown in FIG. 3. Slot 21 in FIG. 4, and another slot 21 on the back side (not shown), together provide a taper candle 16 advancing means from the storage chamber of container 10 up through vertical tube 18. The pair of slots 21 permit finger manipulation of taper strand 16 in vertical tube 18.

A unique aspect of the present invention is the provision of taper candle 16 which is composed of cellulosic fibers which have a content of a chemically-bound air freshener constituent.

The term "chemically-bound" as employed herein refers to a covalent bond between a cellulose polymer chain and an air freshener molecule, such as an ether or ester linkage. The Degree of Substitution (D.S.) can be between about 0.05–3.

The term "air-freshener" as employed herein is meant to include fragrances such as geraniol, insect repellants such as citronellal, and therapeutic agents such as menthol.

An air freshener constituent of a present invention taper candle can be any inherently volatile organic compound which is capable of being covalently linked to a cellulosic matrix by chemical reaction.

Suitable volatile air freshener compounds include alcohols such as undecanol, 4-isopropyl-cyclohexanol, geraniol, linalool, citronellol, farnesol, menthol, 3-trans-isocamphylcyclohexanol, benzyl alcohol, 2-phenylethyl alcohol, 3-phenyl-propanol, 3-methyl-5-phenylpentanol, cinnamic alcohol, isoborneol, thymol, eugenol, isoeugenol, anise alcohol, methyl salicylate, and the like.

Other suitable air freshener compounds include aldehydes and ketones such as hexanal, decanal, 2-methyldecanal, trans-2-hexenal, acetoin, diacetyl, geranial, citronellal, methoxydihydro-citronellal, menthone, carvone, camphor, fenchone, ionone, irone, damascone, cedryl methyl ketone, muscone, civetone, 2,4-dimethyl-3-cyclohexene carboxaldehyde, 2-heptylcyclo-pentanone, cisjasmone, dihydrojasmone, cyclopentadecanone, benzaldehyde, phenylacetaldehyde, dihydrocinnamaldehyde, cinnamaldehyde, α-amylcinnamaldehyde, acetophenone, benzylacetone, benzophenone, piperonal, and the like.

Other suitable air freshener compounds include esters such as trans-2-hexenyl acetate, allyl 3-cyclohexylpropionate, methyl cinnamate, benzyl cinnamate, phenylethyl cinnamate, and the like.

The chemical-bonding of an alcohol air freshener such as geraniol or menthol to a cellulose polymer can be accomplished by the formation of a carbonate ester linkage:

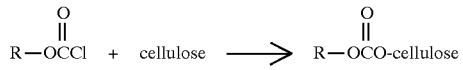

The reaction proceeds readily in the presence of a basic reagent such as sodium hydroxide or an organic amine. The production of cellulose carbonates are described in publications such as U.S. Pat. No. 3,705,890 and U.S. Pat. No. 5,068,321; incorporated by reference.

Another chemical means for forming a linkage between an alcohol air freshener and a cellulose polymer is by the use of an alcohol epichlorohydrin derivative under alkaline reaction conditions.

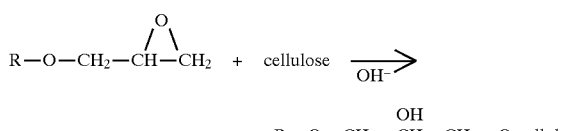

The chemical-bonding of an aldehyde such as citronellal or a ketone such as fenchone to a cellulose polymer can be accomplished by the formation of a hemiacetal (ketal) and/or acetal (ketal) linkage under acidic conditions:

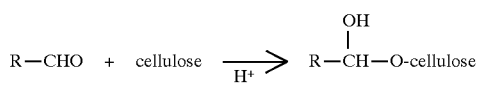

-continued

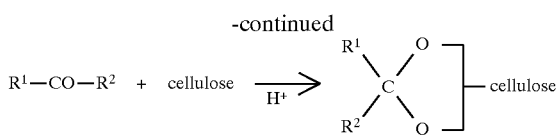

The chemical bonding of an ester such as phenylethyl cinnamate air freshener to a cellulose polymer can be accomplished by a Michael addition reaction under alkaline conditions:

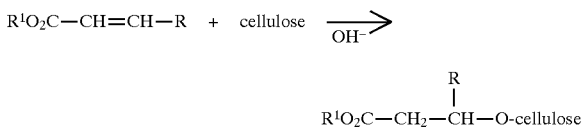

The Michael addition reaction is described in publications such as U.S. Pat. No. 2,415,040 and U.S. Pat. No. 5,569,779; incorporated by reference.

The chemical-bonding of an air freshener constituent to a cellulosic matrix in present invention taper candle 16 provides significant advantages not previously contemplated by the prior art.

The air freshener constituent is released only when the taper candle 16 is being combusted. The air freshener is released by pyrolysis at a sustained constant rate. When the air freshener constituent had, for example, an alcohol group, a carbonyl group, or an olefin group, prior to being chemically bound to the cellulosic matrix, it can possibly have the group reconstituted upon release.

The amount of air freshener constituent which is chemically-bound can be predetermined within a D.S. range between about 0.05–3 by selected synthesis conditions.

Because the air freshener constituent is chemically-bound, there is no premature loss of air freshener by migration and evaporation.

Another essential component of taper candle 16 is a combustible encapsulant ingredient, such as candlewax, organic polymer, cellulose derivative, or the like. Taper candle 16 can have a combustible encapsulant ingredient content between about 5–90 weight percent.

A candlewax encapsulant ingredient can be selected from commercially available wax media and adjuvants, such as beeswax, paraffin wax, montan wax, carnauba wax, microcrystalline wax, fatty alcohols, fatty acids, fatty esters, and the like.

A candlewax encapsulant ingredient can be combined with the cellulosic matrix of taper candle 16 by impregnation of the cellulosic matrix with a candlewax melt, or by compression or extrusion molding of the encapsulant and cellulosic matrix components.

An organic polymer type of combustible encapsulant ingredient preferably is selected from the class of thermoplastic resins which in general are adapted for fiber-formation by processes such as extrusion or compression molding. It is preferred that the polymer is composed of elements which do not convert into noxious vapors under taper candle combustion conditions, such as carbon, hydrogen and oxygen.

Suitable fiber-forming polymers include hydrocarbyl polyolefinic derivatives such as low and high density polyethylene, low and high density polypropylene, polybutene, polystyrene, and the like.

Other types of suitable polymers include polyvinyl acetate, and acrylate resins such as polymethyl acrylate, polymethyl methacrylate, polybutyl methacrylate, poly (ethyl acrylate/ethylene), and the like.

Other preferred types of polymers include cellulosic derivatives such as cellulose acetate, methylcellulose, ethylcellulose, and the like.

Other types of polymers such as thermoset resins can be utilized by pressure molding a resin powder and the air freshener-containing cellulosic matrix.

Taper candle 16 can be produced in a continuous process, such as by extrusion molding of a combustible encapsulant sheath on the air freshener-containing cellulosic matrix in strand form. Equipment and processes having application for this type of extrusion molding of an invention taper candle product are described in publications such as U.S. Pat. Nos. 2,679,069; 3,461,197; 4,435,348; 4,713,139; and 5,529,652; incorporated by reference.

A present invention air freshener dispenser device is easily assembled from inexpensive materials, and it is safely disposable after usage.

A present invention air freshener dispenser device with its taper candle feature is cleaner and less hazardous than a conventional candle in home use, since the taper candle can burn with essentially no formation of a spillable pool of melted combustible fluid such as wax.

As another advantage, a selected length of extended taper candle can be utilized for a predetermined burn period, which then is terminated by self-extinguishment of the taper candle.

A large supply of a flexible taper candle strand can be accommodated in the storage chamber of a present invention air freshener dispenser device, and it can serve for an extended period of frequent use.

The following examples are further illustrative of the present invention. The components and specific ingredients are presented as being typical, and various modifications can be derived in view of the foregoing disclosure within the scope of the invention.

EXAMPLE I

This Example illustrates the preparation of geraniol glycidyl ether.

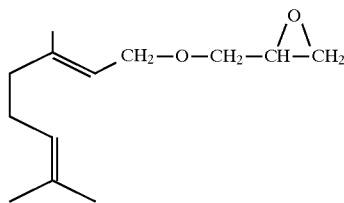

Geraniol (100 g) is added dropwise to a stirred mixture of 50% aqueous sodium hydroxide (300 mL), epichlorohydrin (300 g), and tetrabutylammonium hydrogen sulfate (60 g) with cooling to maintain a temperature of 20° C.

After a reaction period of 18 hours, the mixture is poured into water (one liter), and the aqueous medium is extracted with chloroform. The extract layer is washed with water, dried over sodium sulfate and filtered, and an oil product is recovered after solvent evaporation. NMR and IR confirm the structure.

EXAMPLE II

This Example illustrates the preparation of an air freshener-substituted taper candle in accordance with the present invention.

A reactor equipped with a reflux condenser and stirrer is charged with hexane (one liter), caustic solution (20 g of 50% aqueous sodium hydroxide), and a strand of braided cotton (0.3 cm diameter; 30 cm length). The mixture is stirred for 30 minutes at 25° C. under a nitrogen atmosphere.

Geraniol glycidyl ether (50 g) is added to the slurry, and the resulting reaction mixture is heated at 80° C. for 10 hours. The mixture then is cooled to room temperature, neutralized with glacial acetic acid, and filtered.

The recovered cotton strand is washed with acetone and then with water. After drying, solid state NMR indicates that the cellulosic matrix of the cotton strand has a D.S. of 0.38.

The cotton strand is impregnated with melted paraffin wax (MP 55° C.). The resultant flexible taper candle has a wax content of about 30 weight percent.

When the taper candle is ignited, it burns with a flame combustion, and releases a flowery-rose note which is characteristic of geraniol.

Similar combustion results are obtained when the taper candle is a component of an invention dispenser device as illustrated in FIGS. 1–4.

EXAMPLE III

This Example illustrates the preparation of a present invention taper candle which is substituted with a fragrance mixture.

Following the general procedure of Example I, glycidyl ethers are formed with the constituents of a perfume oil:

|  | Parts |
| --- | --- |
| hydroxycitronellal | 18.0 |
| cinnamyl alcohol | 1.7 |
| terpineol | 8.0 |
| benzyl alcohol | 18.0 |
| phenethyl alcohol | 20.0 |
| linalool | 2.0 |

In a manner similar to that described in Example II, a strand of braided cotton is treated with the glycidyl ether mixture to chemically bind the fragrance constituents to the cellulosic matrix of the braided cotton (a D.S. of 0.6).

The cotton strand is dipped in melted beeswax (MP 66° C.) until a flexible taper candle is formed which has a wax content of about 80 weight percent.

When the taper candle is ignited, it burns with a flame combustion, and releases a flowery lilac note into the atmosphere.

EXAMPLE IV

This Example illustrates the preparation of a present invention taper candle which is substituted with a fragrance mixture.

Following the general procedure of Example I, glycidyl ethers are formed with the constituents of a perfume oil:

|  | Parts |
| --- | --- |
| hydroxycitronellal | 50.00 |
| benzyl alcohol | 4.0 |
| geraniol | 3.0 |
| citronellol | 3.0 |
| linalool | 3.0 |

In a manner similar to that described in Example II, a long strand of braided cotton (200 cm) is treated with the glycidyl ether mixture to chemically bind the fragrance constituents to the cellulose matrix of the braided cotton (D.S. of 2.2). Dimethylformamide and lithium chloride are employed as additional ingredients in the reaction process to increase the D.S. in the cellulose matrix.

Polyethylene powder (MP 120° C.) is charged to an extruder, and the cotton strand is passed through the extruder with the polyethylene powder under heat and pressure to form a continuous polymer sheath coating on the cotton strand. The resultant flexible taper candle has a polyethylene weight content of about 18 weight percent, and a 0.45 cm diameter.

When the taper candle is ignited, it burns with a slow flame combustion, and releases a lily-of-the-valley note into the atmosphere.

EXAMPLE V

This Example illustrates the preparation of menthyl chloroformate.

A reactor in a dry-ice/acetone bath (−75° C.) is charged with liquid phosgene (117 g). Menthol (130 g), dissolved in 150 mL of cyclopentane, is added dropwise to the phosgene with stirring. The reaction medium is refluxed for six hours at room temperature.

The excess phosgene and cyclopentane are removed under reduced pressure. The recovered menthyl chloroformate is dissolved in diethyl ether (60 mL), and the solution is washed with aqueous sodium bicarbonate, and then with distilled water. The liquid medium is dried over sodium sulfate, and the solvent is removed under reduced pressure to yield a purified menthyl chloroformate.

EXAMPLE VI

This Example illustrates the preparation of a menthyl carbonate ester-substituted taper candle in accordance with the present invention.

A 600 g strand of multi-filament rayon (North American Rayon, yarn 4321) is suspended in a blend of pyridine (2300 g) and benzene (4 liters), and the admixture is stirred for 20 hours at room temperature.

A 1800 g quantity of menthyl chloroformate is added dropwise to the stirred reaction medium at room temperature. The stirring is continued for 12 hours at a reaction medium temperature of 85° C. After cooling and filtering, the recovered rayon strand product is washed with benzene, then with isopropanol and with water. The rayon strand product has a menthyl carbonate D.S. of 1.3.

The rayon strand is impregnated with melted paraffin wax/10% microcrystalline wax (MP 68°–71° C.). The resultant flexible taper candle has a wax content of about 26 weight percent.

Flame combustion of the taper candle releases a readily detectable menthol scent into the atmosphere.

EXAMPLE VII

This Example illustrates the preparation of a citronellal acetal-substituted taper candle in accordance with the present invention.

A reactor is equipped with a stirrer and a reflux condenser having a water-removal unit. The reactor is charged with benzene (600 mL), p-toluenesulfonic acid (75 mg), citronellal (75 g) and a strand of braided cotton (0.3 cm diameter; 200 cm length).

The admixture is heated at reflux with stirring, and continued until no more water is entrained as an azeotrope.

After cooling, the acid catalyst is neutralized with ammonium hydroxide. The mixture is filtered, and the recovered cotton strand is washed with water. After drying, solid state NMR indicates that the cellulosic matrix of the cotton strand has a D.S. of about 0.2.

Polypropylene powder (M.P. 110° C.) is charged to an extruder, and the cotton strand is passed through the extruder with the polypropylene powder under heat and pressure to form a polymer sheath on the cotton strand. The resultant flexible taper candle has a polypropylene content of about 48 weight percent, and a 0.55 cm diameter.

Flame combustion of the taper candle releases a mild citronellal scent into the atmosphere.

What is claimed is:

1. An air freshener dispenser device which comprises:
   a container having an interior storage chamber and an opening;
   a partition across the opening of the container, the partition having a bore therethrough;
   a bore tube extending from the bore of the partition to form a passage out of the container storage chamber; and
   an elongated taper candle strand comprising a cellulosic matrix, molecules of an air freshener constituent being covalently bonded to the cellulosic matrix, and a combustible encapsulant ingredient combined with the cellulosic matrix, the taper candle strand being disposed within the container storage chamber and extending through the bore tube so that a portion of the taper candle strand is exposed,
   wherein combustion of the exposed portion of the taper candle strand releases the air freshener constituent therefrom into the atmosphere.

2. A dispenser device in accordance with claim 1, further comprising a lid that is removably securable to the container to enclose the tube and partition.

3. A dispenser device in accordance with claim 1, further comprising means for advancing the taper candle upward through the tube.

4. A dispenser device in accordance with claim 1, further comprising an ash receptacle disposed about the tube.

5. A dispenser device in accordance with claim 2, wherein the container has an annular cross section with a diameter between about two to five centimeters, and the dispenser device has a height of between about six to twelve centimeters.

6. A dispenser device in accordance with claim 1, wherein the taper candle has an annular cross-section with a diameter between about 3–8 millimeters.

7. A dispenser device in accordance with claim 1, wherein the taper candle has a length of at least about 20 centimeters.

8. A dispenser device in accordance with claim 1, wherein the taper candle has a combustible encapsulant ingredient content between about 5–90 weight percent.

9. A dispenser device in accordance with claim 1, wherein the combustible encapsulant ingredient of the taper candle comprises candlewax.

10. A dispenser device in accordance with claim 1, wherein the combustible encapsulant ingredient of the taper candle comprises an organic polymer.

11. A dispenser device in accordance with claim 1, wherein the combustible encapsulant ingredient of the taper candle comprises a cellulose derivative.

12. A dispenser device according to claim 1, wherein the combustible encapsulant ingredient of the taper candle comprises a polymer selected from the group consisting of polyethylene and polypropylene.

13. A dispenser device in accordance with claim 1, wherein the combustible encapsulant ingredient of the taper candle comprises cellulose acetate.

14. A dispenser device in accordance with claim 1, wherein the degree of substitution of the air freshener in the cellulosic matrix of the taper candle is between about 0.05–3.

15. A dispenser device in accordance with claim 1, wherein the air freshener constituent is chemically-bound to the cellulosic matrix of the taper candle by an ether linkage.

16. A dispenser device in accordance with claim 1, wherein the air freshener constituent is chemically-bound to the cellulosic matrix of the taper candle by an ester linkage.

17. A dispenser device in accordance with claim 1, wherein the air freshener constituent after release from the cellulosic matrix of the taper candle has a reconstituted alcohol group.

18. A dispenser device in accordance with claim 1, wherein the air freshener constituent after release from the cellulosic matrix of the taper candle has a reconstituted carbonyl group.

19. A dispenser device in accordance with claim 1 wherein the air freshener constituent after release from the cellulosic matrix of the taper candle includes an olefin group.

20. A dispenser device in accordance with claim 1, wherein the air freshener constituent after release from the cellulosic matrix of the taper candle is a fragrance composition.

21. A dispenser device in accordance with claim 1, wherein the air freshener constituent after release from the cellulosic matrix of the taper candle is an insect repellant composition.

22. A dispenser device in accordance with claim 1, wherein the air freshener constituent after release from the cellulosic matrix of the taper candle is a therapeutic composition.

23. A dispenser device in accordance with claim 1, wherein the air freshener released from the taper candle comprises geraniol.

24. A dispenser device in accordance with claim 1, wherein the air freshener released from the taper candle comprises citronellal.

25. A dispenser device in accordance with claim 1, wherein the air freshener released from the taper candle comprises menthol.

26. A dispenser device according to claim 1, wherein the cellulosic matrix of the taper candle is a fiber selected from the group consisting of cotton and rayon.

27. A dispenser device in accordance with claim 1, wherein the taper candle after ignition burns with flame combustion.

28. A taper candle strand comprising:
   a cellulosic matrix to which molecules of an air freshener constituent are covalently bonded; and
   a combustible encapsulant ingredient combined with the cellulosic matrix;
   wherein combustion of the taper candle strand results in release of the air freshener constituent into the atmosphere.

29. A taper candle strand in accordance with claim 28, which has a combustible encapsulant ingredient content between about 5–90 weight percent.

30. A taper candle strand in accordance with claim 28, wherein the combustible encapsulant ingredient comprises candlewax.

31. A taper candle strand in accordance with claim 28, wherein the combustible encapsulant ingredient comprises an organic polymer.

32. A taper candle product in accordance with claim 28, wherein the combustible encapsulant ingredient comprises a cellulose derivative.

33. A taper candle strand in accordance with claim 28, wherein the combustible encapsulant ingredient comprises a polymer selected from the group consisting of polyethylene and polypropylene.

34. A taper candle strand in accordance with claim 28, wherein the combustible encapsulant ingredient comprises cellulose acetate.

35. A taper candle strand in accordance with claim 28, wherein the degree of substitution of air freshener in the cellulosic matrix is between about 0.05–3.

36. A taper candle strand in accordance with claim 28, wherein the air freshener constituent after release from the cellulosic matrix is a fragrance composition.

37. A taper candle strand in accordance with claim 28, wherein the air freshener constituent after release from the cellulosic matrix is an insect repellant composition.

38. A taper candle strand in accordance with claim 28, wherein the air freshener constituent after release from the cellulosic matrix is a therapeutic composition.

* * * * *

UNITED STATES PATENT AND TRADEMARK OFFICE
CERTIFICATE OF CORRECTION

Patent No.  : 5,876,706
Dated       : Mar. 2, 1999
Inventor    : Judith R. Zaunbrecher It is certified that an error appears in the above-identified patent and that said Letters Patent is hereby corrected as shown below:

<u>In Claims</u>:

Claim 32, line 1, please delete "product" and substitute --strand--.

Signed and Sealed this

Twenty-seventh Day of March, 2001

*Attest:*

NICHOLAS P. GODICI

*Attesting Officer*   Acting Director of the United States Patent and Trademark Office